United States Patent
Safai et al.

(10) Patent No.: US 11,198,261 B1
(45) Date of Patent: Dec. 14, 2021

(54) SYSTEMS AND METHODS FOR DEPOSITION AND HIGH-FREQUENCY MICROWAVE INSPECTION OF UNCURED FIBER-REINFORCED POLYMERIC MATERIALS

(71) Applicant: The Boeing Company, Chicago, IL (US)

(72) Inventors: Morteza Safai, Newcastle, WA (US); Gary E. Georgeson, Tacoma, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 16/892,065

(22) Filed: Jun. 3, 2020

(51) Int. Cl.
*B29C 70/54* (2006.01)
*G01N 22/02* (2006.01)
*B29C 70/38* (2006.01)

(52) U.S. Cl.
CPC ............ *B29C 70/54* (2013.01); *B29C 70/384* (2013.01); *G01N 22/02* (2013.01)

(58) Field of Classification Search
CPC ........ B29C 70/54; B29C 70/384; G01N 22/02
See application file for complete search history.

(56) References Cited

U.S. PATENT DOCUMENTS

| | | | |
|---|---|---|---|
| 9,404,904 B2 | 8/2016 | Puckett et al. | |
| 9,827,720 B2 | 11/2017 | Heath et al. | |
| 10,119,866 B2 | 11/2018 | Thompson et al. | |
| 2017/0160139 A1 | 6/2017 | Holmes et al. | |
| 2018/0093433 A1* | 4/2018 | Treiber | B29C 70/384 |
| 2019/0383759 A1 | 12/2019 | Johnson et al. | |
| 2021/0206123 A1* | 7/2021 | Boyle | B29C 70/384 |

* cited by examiner

*Primary Examiner* — Vishal I Patel
(74) *Attorney, Agent, or Firm* — Kunzler Bean & Adamson

(57) ABSTRACT

Disclosed herein is a system that comprises a deposition head configured to deposit multiple tows in a stacked configuration one layer at a time. Each tow of the multiple tows is a currently-applied tow when the tow is a most-recently deposited tow of the multiple tows and a tow of the multiple tows is a covered tow when the tow is directly covered by the currently-applied tow. The system also comprises a probe head, configured to move along and be spatially offset from the currently-applied tow after deposition of the currently-applied tow. The probe head is further configured to transmit an incident microwave beam into the currently-applied tow as the probe head moves along the currently-applied tow. The incident microwave beam has a frequency low enough to pass entirely through the currently-applied tow and high enough to pass entirely through no more than the currently-applied tow and the covered tow.

20 Claims, 11 Drawing Sheets

SYSTEMS AND METHODS FOR DEPOSITION AND HIGH-FREQUENCY MICROWAVE INSPECTION OF UNCURED FIBER-REINFORCED POLYMERIC MATERIALS

FIELD

This disclosure relates generally to the manufacturing and inspection of parts, and more particularly to depositing uncured fiber-reinforced polymeric material and inspecting the uncured fiber-reinforced polymeric material using high-frequency microwaves.

BACKGROUND

The inspection of aerospace composite structures can be costly and time-consuming. Some aerospace composite structures are manufactured by the automated placement of fiber-reinforced polymeric materials using various tape or ply lay-up processes. Monitoring the fiber-reinforced polymeric material, including the placement of the material, during the lay-up process to identify and limit material and placement defects and to improve the overall manufacturing process is needed.

Most monitoring techniques identify defects after the fiber-reinforced polymeric material is cured. Some monitoring techniques are used to identify and limit defects in the fiber-reinforced polymeric material before the material is cured. However, conventional monitoring techniques to identify and limit defects in uncured fiber-reinforced polymeric material suffer from several shortcomings, such as cost, speed, lack of sensitivity, and edge effect issues.

SUMMARY

The subject matter of the present application provides examples of systems and methods for depositing and inspecting uncured fiber-reinforced polymeric materials that overcome at least some of the above-discussed shortcomings of prior art techniques. Accordingly, the subject matter of the present application has been developed in response to the present state of the art, and in particular, in response to shortcomings of conventional monitoring techniques for identifying and limiting defects in uncured fiber-reinforced polymeric material.

Disclosed herein is a system that comprises a deposition head that is configured to deposit multiple tows of uncured fiber-reinforced polymeric material in a stacked configuration one layer at a time. Each tow of the multiple tows is a currently-applied tow when the tow is a most-recently deposited tow of the multiple tows and a tow of the multiple tows is a covered tow when the tow is directly covered by the currently-applied tow. The system also comprises a probe head that is configured to move along and be spatially offset from the currently-applied tow after deposition of the currently-applied tow. The probe head is further configured to transmit an incident microwave beam into the currently-applied tow as the probe head moves along the currently-applied tow. The incident microwave beam has a frequency low enough to pass entirely through the currently-applied tow and high enough to pass entirely through no more than the currently-applied tow and the covered tow. The preceding subject matter of this paragraph characterizes example 1 of the present disclosure.

The frequency of the incident microwave beam is between 50 GHz and 100 GHz. The preceding subject matter of this paragraph characterizes example 2 of the present disclosure, wherein example 2 also includes the subject matter according to example 1, above.

The frequency of the incident microwave beam is high enough to pass entirely through no more than the currently-applied tow and a stack interface between the currently-applied tow and the covered tow. The preceding subject matter of this paragraph characterizes example 3 of the present disclosure, wherein example 3 also includes the subject matter according to any one of examples 1-2, above.

The probe head comprises a linear phased array of microwave transmitters. Each one of the microwave transmitters generates a microwave signal. The incident microwave beam comprises a combination of the microwave signals generated by the linear phased array of microwave transmitters. The linear phased array is configured to phase shift the generation of the microwave signals. The probe head is configured to move the incident microwave beam laterally across a width of the currently-applied tow, in a direction substantially perpendicular to movement of the probe head along the currently-applied tow, by selectively controlling the linear phased array to change the phase shift of the generation of the microwave signals. The preceding subject matter of this paragraph characterizes example 4 of the present disclosure, wherein example 4 also includes the subject matter according to any one of examples 1-3, above.

The probe head further comprises at least one edge detector, which is configured to detect at least one edge of the currently-applied tow as the probe head moves along the currently-applied tow. The probe head is further configured to prevent movement of the incident microwave beam beyond the at least one edge in response to detection of the at least one edge of the currently-applied tow. The preceding subject matter of this paragraph characterizes example 5 of the present disclosure, wherein example 5 also includes the subject matter according to example 4, above.

The deposition head is further configured to deposit multiple tows of uncured fiber-reinforced polymeric material in a side-by-side arrangement one layer at a time. The stacked configuration further comprises multiple layers of tows in the side-by-side arrangement. The at least one edge detector is further configured to detect the edge of one currently-applied tow, of a currently-applied layer of tows in the side-by-side arrangement, and the edge of another currently-applied tow, of the currently-applied layer of tows in the side-by-side arrangement. The probe head is further configured to prevent movement of the incident microwave beam beyond the one edge of the one currently-applied tow, of the currently-applied layer of tows in the side-by-side arrangement, and the edge of the other currently-applied tow, of the currently-applied layer of tows in the side-by-side arrangement, in response to detection of the edge of the one currently-applied tow, of the currently-applied layer of tows in the side-by-side arrangement, and the edge of the other currently-applied tow, of the currently-applied layer of tows in the side-by-side arrangement. The preceding subject matter of this paragraph characterizes example 6 of the present disclosure, wherein example 6 also includes the subject matter according to example 5, above.

The probe head further comprises a laser profilometer configured to transmit a laser beam to the currently-applied tow and determine profile characteristics of the currently-applied tow based on a displacement of the laser beam after impacting the currently-applied tow. The preceding subject matter of this paragraph characterizes example 7 of the present disclosure, wherein example 7 also includes the subject matter according to any one of examples 1-6, above.

The deposition head moves along a deposition path to deposit the multiple tows of uncured fiber-reinforced polymeric material in the stacked configuration. The probe head is non-movably affixed to the deposition head such that the probe head moves along the deposition path with the deposition head. The preceding subject matter of this paragraph characterizes example 8 of the present disclosure, wherein example 8 also includes the subject matter according to any one of examples 1-7, above.

The system further comprises a robot. The deposition head is coupled to the robot such that the deposition head is movable, to deposit the multiple tows in the stacked configuration, by the robot. The probe head is coupled to the robot such that the probe head is movable, along each tow of the of the multiple tows, by the robot. The preceding subject matter of this paragraph characterizes example 9 of the present disclosure, wherein example 9 also includes the subject matter according to any one of examples 1-8, above.

The system further comprises a robot and a second robot, which is independently movable relative to the robot. The deposition head is coupled to the robot such that the deposition head is movable, to deposit the multiple tows in the stacked configuration, by the robot. The probe head is coupled to the second robot such that the probe head is movable, along each tow of the of the multiple tows, by the second robot. The preceding subject matter of this paragraph characterizes example 10 of the present disclosure, wherein example 10 also includes the subject matter according to any one of examples 1-8, above.

The probe head is further configured to detect a reflected microwave beam. The reflected microwave beam comprises at least a portion of the incident microwave beam reflected from at least one of the currently-applied tow or a stack interface. The preceding subject matter of this paragraph characterizes example 11 of the present disclosure, wherein example 11 also includes the subject matter according to any one of examples 1-10, above.

The system further comprises a controller configured to determine a dielectric response of at least one of the currently-applied tow or the stack interface based on the reflected microwave beam. The preceding subject matter of this paragraph characterizes example 12 of the present disclosure, wherein example 12 also includes the subject matter according to example 11, above.

The probe head further comprises at least one of an infrared camera configured to generate a thermal image of the currently-applied tow based on infrared radiation from the currently-applied tow, or a visual camera configured to generate a visual image of the currently-applied tow. The preceding subject matter of this paragraph characterizes example 13 of the present disclosure, wherein example 13 also includes the subject matter according to any one of examples 1-12, above.

Further disclosed herein is a probe head. The probe head comprises a microwave sensor that is configured to transmit an incident microwave beam into a currently-applied tow, forming part of a stacked configuration of multiple tows of uncured fiber-reinforced polymeric material, as the microwave sensor moves along the currently-applied tow. The incident microwave beam has a frequency low enough to pass entirely through currently-applied tow and high enough to pass entirely through no more than the currently-applied tow and a covered tow on which the currently-applied tow is directly stacked. The microwave sensor further comprises a linear phased array of microwave transmitters. Each one of the microwave transmitters generates a microwave signal. The incident microwave beam comprises a combination of the microwave signals generated by the linear phased array of microwave transmitters. The linear phased array is configured to phase shift the generation of the microwave signals. The microwave sensor is configured to move the incident microwave beam laterally across a width of the currently-applied tow, in a direction perpendicular to movement of the probe head along the currently-applied tow, by selectively controlling the linear phased array to change the phase shift of the generation of the microwave signals. The probe head also comprises at least one edge detector, configured to detect at least one edge of the currently-applied tow as the at least one edge detector moves along the currently-applied tow. The microwave sensor is further configured to limit movement of the incident microwave beam beyond the at least one edge in response to detection of the at least one edge of the currently-applied tow. The preceding subject matter of this paragraph characterizes example 14 of the present disclosure.

The probe head further comprises at least one of an infrared camera or a laser profilometer. The infrared camera is configured to generate a thermal image of the currently-applied tow based on infrared radiation from the currently-applied tow. The laser profilometer is configured to transmit a laser beam to the currently-applied tow and determine profile characteristics of the currently-applied tow based on a displacement of the laser beam upon impacting the currently-applied tow. The preceding subject matter of this paragraph characterizes example 15 of the present disclosure, wherein example 15 also includes the subject matter according to example 14, above.

Additionally disclosed herein is a method that comprises depositing a currently-applied tow, made of uncured fiber-reinforced polymeric material, onto an object or onto a covered tow to form a stacked configuration with the covered tow. The method also comprises transmitting an incident microwave beam into the currently-applied tow at locations along the currently-applied tow after deposition of the currently-applied tow. The incident microwave beam has a frequency low enough to pass entirely through the currently-applied tow and high enough to pass entirely through no more than the currently-applied tow and a stack interface between the currently-applied tow and the covered tow. The method further comprises detecting a reflected microwave beam, comprising at least a portion of the incident microwave beam reflected from at least one of the currently-applied tow or the stack interface. The method additionally comprises determining a dielectric response of the currently-applied tow or the stack interface based on the reflected microwave beam. The preceding subject matter of this paragraph characterizes example 16 of the present disclosure.

The method further comprises moving the incident microwave beam laterally across a width of the currently-applied tow. The method also comprises detecting at least one edge of the currently-applied tow at the locations along the currently-applied tow. The method further comprises preventing movement of the incident microwave beam beyond the at least one edge in response to detecting the at least one edge. The preceding subject matter of this paragraph characterizes example 17 of the present disclosure, wherein example 17 also includes the subject matter according to example 16, above.

The step of depositing the currently-applied tow and the step of transmitting the incident microwave beam into the currently-applied tow are performed concurrently. The preceding subject matter of this paragraph characterizes example 18 of the present disclosure, wherein example 18 also includes the subject matter according to any one of examples 16-17, above.

The method further comprises generating a thermal image of the currently-applied tow concurrently with the step of depositing the currently-applied tow and the step of transmitting the incident microwave beam into the currently-applied tow. The thermal image of the currently-applied tow is based on infrared radiation from the currently-applied tow. The preceding subject matter of this paragraph characterizes example 19 of the present disclosure, wherein example 19 also includes the subject matter according to example 18, above.

The method further comprises transmitting a laser beam to the currently-applied tow concurrently with the step of depositing the currently-applied tow and the step of transmitting the incident microwave beam into the currently-applied tow and determining profile characteristics of the currently-applied tow based on a displacement of the laser beam after impacting the currently-applied tow. The preceding subject matter of this paragraph characterizes example 20 of the present disclosure, wherein example 20 also includes the subject matter according to any one of examples 18-19, above.

The described features, structures, advantages, and/or characteristics of the subject matter of the present disclosure may be combined in any suitable manner in one or more examples, including embodiments and/or implementations. In the following description, numerous specific details are provided to impart a thorough understanding of examples of the subject matter of the present disclosure. One skilled in the relevant art will recognize that the subject matter of the present disclosure may be practiced without one or more of the specific features, details, components, materials, and/or methods of a particular example, embodiment, or implementation. In other instances, additional features and advantages may be recognized in certain examples, embodiments, and/or implementations that may not be present in all examples, embodiments, or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific examples that are illustrated in the appended drawings. Understanding that these drawings depict only typical examples of the subject matter, they are not therefore to be considered to be limiting of its scope. The subject matter will be described and explained with additional specificity and detail through the use of the drawings, in which.

DETAILED DESCRIPTION

Reference throughout this specification to "one example," "an example," or similar language means that a particular feature, structure, or characteristic described in connection with the example is included in at least one example of the present disclosure. Appearances of the phrases "in one example," "in an example," and similar language throughout this specification may, but do not necessarily, all refer to the same example. Similarly, the use of the term "implementation" means an implementation having a particular feature, structure, or characteristic described in connection with one or more examples of the present disclosure, however, absent an express correlation to indicate otherwise, an implementation may be associated with one or more examples.

Disclosed herein is a system that deposits multiple tows of uncured fiber-reinforced polymeric material, one layer at a time, to form a stacked configuration of tows. Additionally, the system inspects the tows of the stacked configuration as they are deposited one layer at a time. The system transmits a high-frequency incident microwave beam into a most-recently deposited tow of the stacked configuration and determines the presence of anomalies in the most-recently deposited layer of a tow or tows, the interface between two tows of the most-recently deposited layer if applicable, and/or the interface between one or more tows of the most-recently deposited layer and one or more tows onto which the most-recently deposited layer is deposited. The system enables inspection of pre-cured (i.e., uncured) composite materials as they are laid up in a stacked configuration. Moreover, in some examples, the high range of the frequency of the incident microwave beam ensures the incident microwave beam penetrates only a portion of the stacked configuration up to a predetermined depth, which allows a determination of particular characteristics (e.g., fiber orientation, foreign object debris, laps, gaps, disbands, resin starvations, marcelling, and the like) associated with the predetermined depth of the stacked configuration. The scanned microwave reflection from successive layers of composite material provide ply-by-ply information concerning potential flaw-creating anomalies, which allows on-the-fly adjustments to the current deposition process and/or machine learning for improving future deposition processes.

Figure 1:
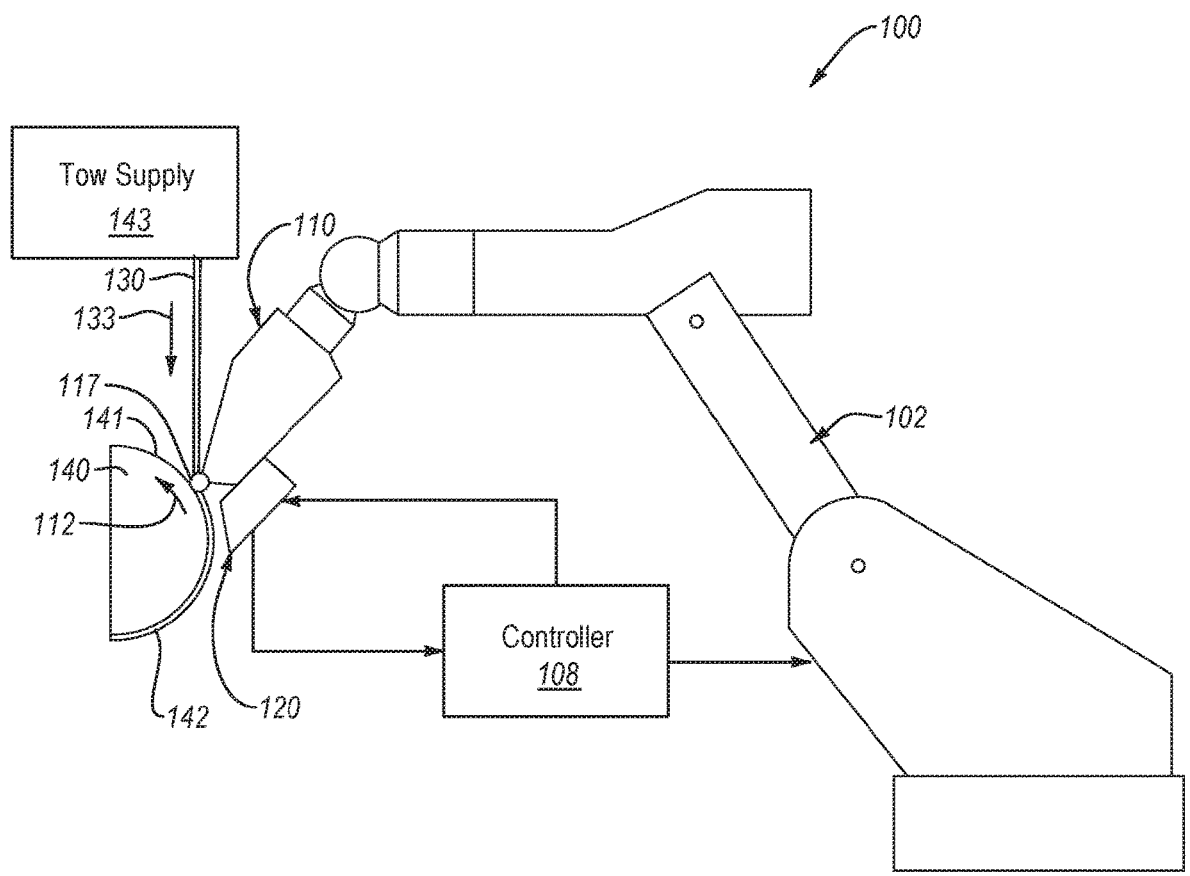
FIG. 1 is a schematic, elevation view of a system for depositing multiple tows of uncured fiber-reinforced polymeric material one layer at a time and inspecting the multiple tows one layer at a time, according to one or more examples of the present disclosure.

Referring to FIG. 1, according to one example, a system 100, for depositing multiple tows 130 of uncured fiber-reinforced polymeric material one layer at a time and inspecting the multiple tows 130 one layer at a time, includes a deposition head 110 and a probe head 120. In the example of FIG. 1, the probe head 120 is non-movably affixed to the deposition head 110 such that the probe head 120 moves as the deposition head 110 moves. In other words, in some examples, the probe head 120 is co-movably coupled to the deposition head 110.

The deposition head 110 is configured to deposit the multiple tows 130 in a stacked configuration 142 one layer at a time. The tows 130 are supplied from a tow supply 143 of the system 100. In some examples, the tow supply 143 includes one or more spools containing an effectually continuous length of uncured fiber-reinforced polymeric material having a set width W. The continuous length of material from the tow supply 143 is cut to length by the deposition head 110 to form the individual tows 130. Alternatively, the tows 130 can be precut to length prior to being introduced to the deposition head 110. Additionally, in certain examples, the tows 130 can be formed from slit tape or include other strips of precured-composite media.

The uncured fiber-reinforced polymeric material of the tows 130 includes fibers, such as carbon fibers, glass fibers, and/or metal fibers, in some examples. The fibers can be unidirectional, multi-directional, or interwoven. The fibers are embedded in a polymeric material, such as resin or epoxy in an uncured (i.e., precured state), to form the tow 130. For example, the tow 130 may be a pre-impregnated carbon fiber tape. Accordingly, each tow 130 may include impregnated fibers with preimpregnated resin. The resin may be a thermoset or thermoplastic material. In one example, the resin is a thermoset resin made of, for example, polyurethanes, polyester, vinylester, epoxy, and the like. In another example, the resin is a thermoplastic resin, such as a polyetheretherketone (PEEK) or polyetherketoneketone (PEKK) material in some examples. In certain examples, the tows 130 have some degree of "tack" or stickiness. In some examples, each tow 130 has a width W of between 0.125 inches, inclusively, and 0.5 inches, inclusively. For example, each tow 130 may have a width W of 0.125 inches, 0.25 inches, or 0.5 inches. In other examples, the tows 130 can have a width W that is less than 0.125 inches or more than 0.5 inches.

According to some examples, the system 100 includes an automated fiber placement system for delivering tows 130 onto a surface 141 of an object 140. The automated fiber placement system includes the deposition head 110 and a robot 102. The deposition head 110 is coupled to and movable by the robot 102. Accordingly, the deposition head 110 functions as an end effector in some examples. In other words, the deposition head 110 is movable by the robot 102, relative to the robot 102, to deliver the tows 130 onto the surface 141. The tow supply 143 can be fixed to the robot 102 and movable with the robot 102. Alternatively, the tow supply 143 physically separated from the robot 102.

The robot 102 can be any of various automated robots. In some examples, the robot 102 includes a footing and multiple articulating members, such as a base that is rotatable relative to the footing about a vertical axis, a connecting arm that is pivotable relative to the base about a horizontal axis, a support arm that is pivotable relative to the connecting arm about a horizontal axis, an end-effector extension arm that is rotatable relative to the support arm about a support axis, an end-effector coupler arm that is pivotable relative to the end-effector extension arm, and an end-effector interface arm that is rotatable and to which the deposition head 110 is co-movably fixed. Accordingly, in some examples, the robot 102 is a 6-axis robot that facilitates motion of the deposition head 110 with 6-degrees of freedom. However, in other examples, the robot 102 can have fewer or more than 6-degrees of freedom.

The surface 141 is the surface of any object 140 onto which the application of the tow 130 is advantageous. In one example, the object 140 is a die or mold and the surface 141 defines a shape of a part to be formed by the die or mold. Accordingly, in certain implementations, the tow 130 is a material tape that is laid up on the surface 141 to form a layer of a stacked configuration 142 to be formed into a part. For example, the surface 141 can be a layup or forming mandrel with a contour representative of an aerodynamic surface. In other examples, the object 140 is a part and the surface 141 is a surface of the part. Accordingly, in certain implementations, the tow 130 is applied directly onto the surface of a part to form the stacked configuration 142 on the part. Accordingly, multiple layers of a tow 130 or tows 130 are formed on top of each other, in the stacked configuration 142, to ultimately form a laminated part after curing the stacked configuration 142.

The deposition head 110 of the system 100 includes an applicator 117 that is configured to apply a single tow 130 or multiple tows 130 onto the surface 141 at a time. Accordingly, the configuration of the applicator 117 is dependent on the material, shape, and number of tows 130 being deposited on a single pass. According to one example, each tow 130 includes material tape and the applicator 117 is a compaction roller. The compaction roller is rotatable about a roller axis to apply tows 130 onto the surface 141. The compaction roller compacts (e.g., compresses) the tows 130 against the surface 141, which facilitates deliverance of the tows 130 onto the surface 141. The robot 102 is operable to translationally move the deposition head 110 in a deposition path 112 such that the applicator 117 also moves along the surface 141 in the deposition path 112. When the surface 141 is contoured, such as shown in FIG. 1, the robot 102 is configured to adjust the position (e.g., height and/or angle) of the applicator 117 to continue moving in the application direction along the contoured portion of the surface 141. Adjustment of the applicator 117 can be made by tilting or raising or lowering the deposition head 110 using one or more articulating members of the robot 102.

The tow 130 or tows 130 are fed to the applicator 117 of the deposition head 110 from the tow supply 143. Although not shown, to help prevent interference (e.g., undesired contact) between the tows 130, the robot 102, and deposition head 110, as the tows 130 are fed to the applicator 117, the tows 130 are threaded through a tow standoff co-movably fixed to the deposition head 110.

Figure 2A:
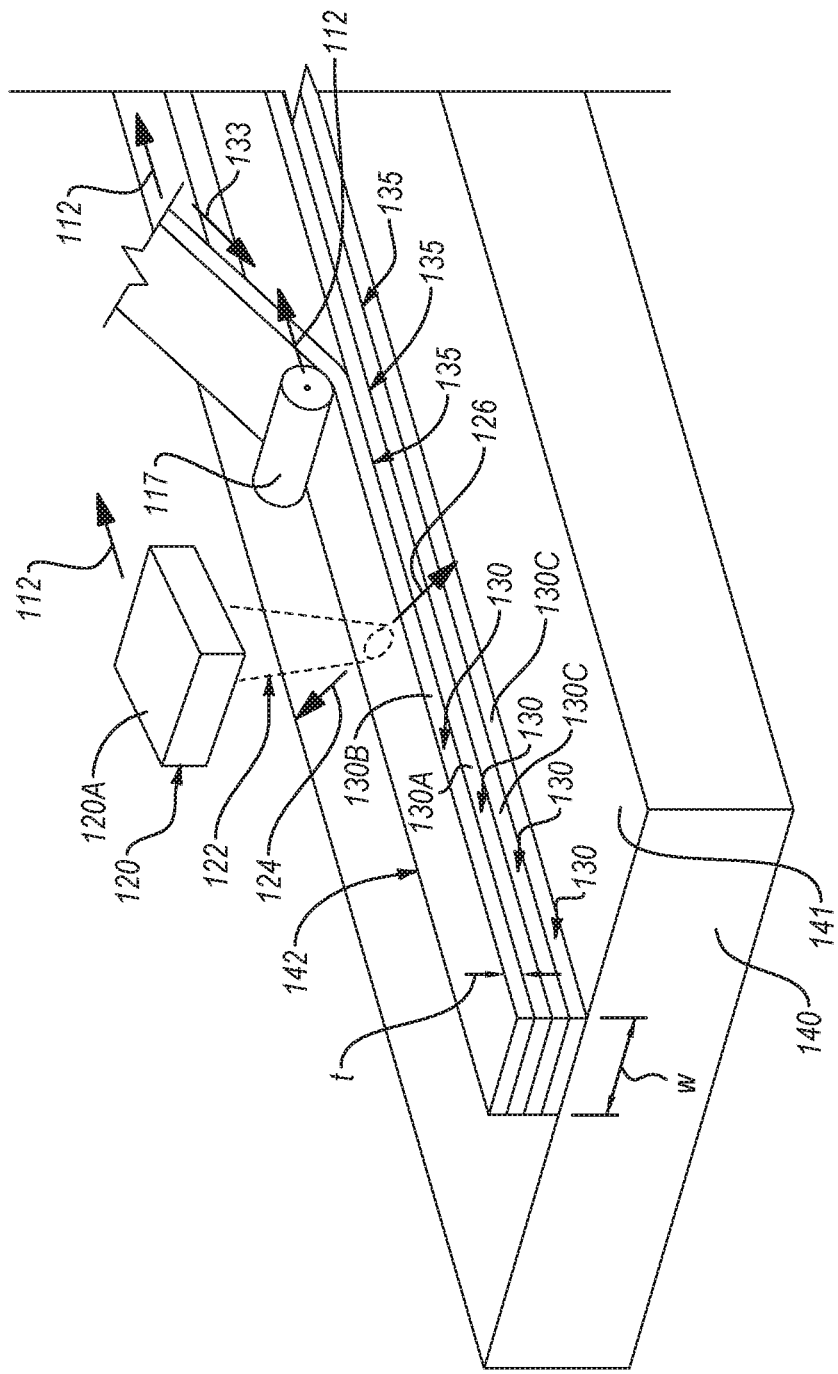
FIG. 2A is a schematic, perspective view of an applicator and a probe head of the system of FIG. 1, shown depositing multiple tows of uncured fiber-reinforced polymeric material in a stacked configuration one tow at a time, according to one or more examples of the present disclosure.

Referring to FIG. 2A, the applicator 117 receives a tow 130 and deposits the tow 130 onto either the surface 141 of the object 140 or a previously deposited tow 130. Each deposited tow 130 in FIG. 2A individually forms a layer of the stacked configuration 142, such that each layer of the stacked configuration 142 has a width equal to the width W of a tow 130. As an example, the stacked configuration 142 of FIG. 2A has four layers with each layer being formed by a single tow 130.

Figure 2B:
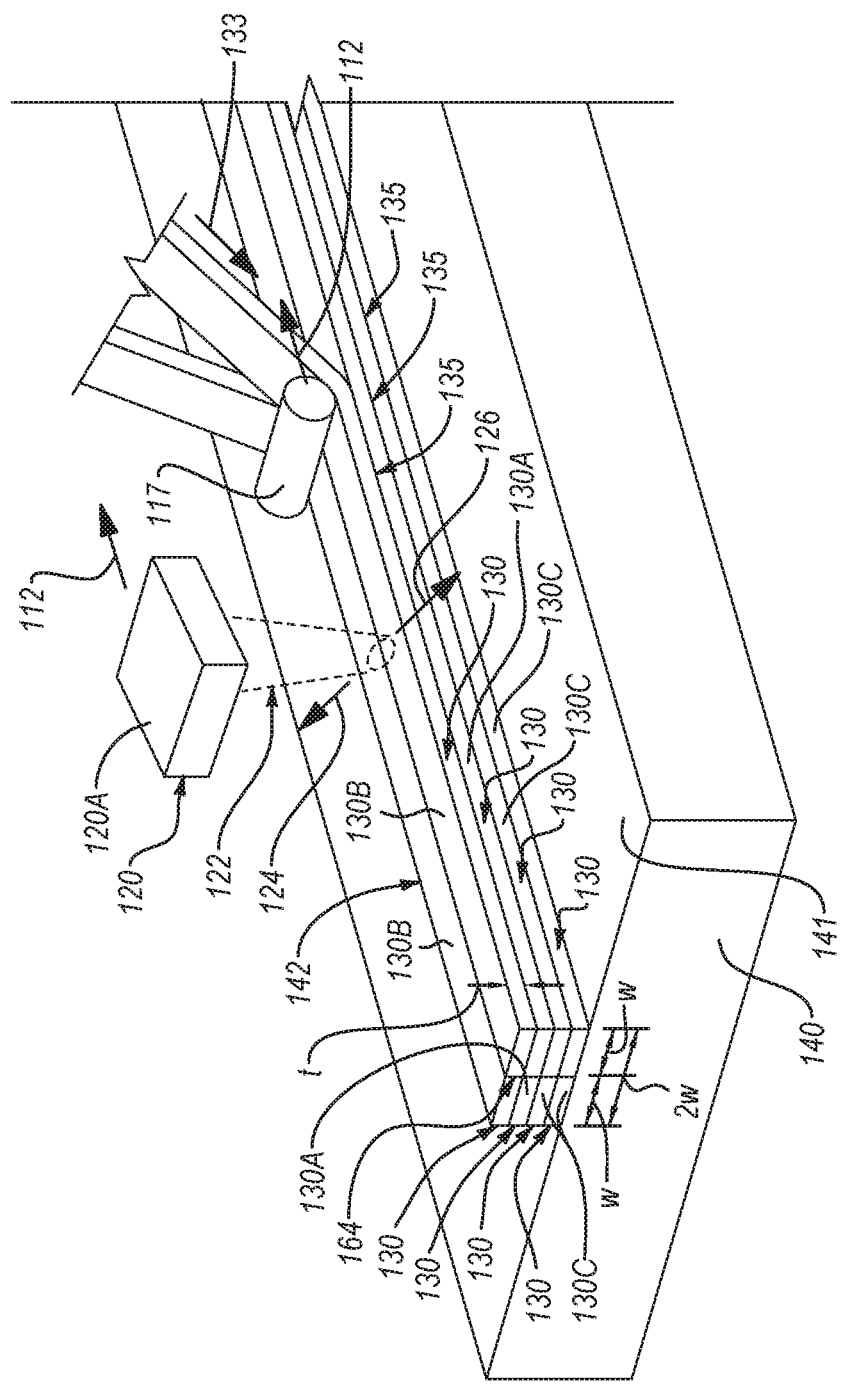
FIG. 2B is a schematic, perspective view of an applicator and a probe head of the system of FIG. 1, shown depositing multiple tows of uncured fiber-reinforced polymeric material in a stacked configuration multiple tows at a time, according to one or more examples of the present disclosure.

Alternatively, as shown in FIG. 2B, the applicator 117 receives multiple tows 130 and concurrently deposits the multiple tows 130, in a side-by-side arrangement, onto either the surface 141 of the object 140 or previously deposited tows 130. The multiple tows 130 in FIG. 2B, deposited concurrently in the side-by-side arrangement, collectively form a layer of the stacked configuration 142. As used herein, the most recently applied layer of a tow 130 or tows 130 is a currently-applied layer and the layer covered by the currently-applied layer is a covered layer. Each layer of the stacked configuration 142 has a width equal to the number of side-by-side tows 130 multiplied by the width W of the tows 130. As an example, the stacked configuration 142 of FIG. 2B has four layers with each layer being formed by two side-by-side tows 130. Accordingly, the stacked configuration 142 in FIG. 2B has a width equal to two widths W of a tow 130 or 2W. Of course, in other examples, more than two tows 130 can be concurrently deposited in a side-by-side manner by the applicator 117 such that each layer of the stacked configuration 142 has more than two tows 130 in a side-by-side arrangement. A side interface 164 is defined between interior edges 137 of side-by-side ones of the tows 130. The side interface 164 becomes a bonding interface between the side-by-side ones of the tows 130 when the stacked configuration 142 is cured. Two tows 130 in a side-by-side arrangement that share a side interface 164 can be considered laterally-adjacent tows.

Figure 3A:
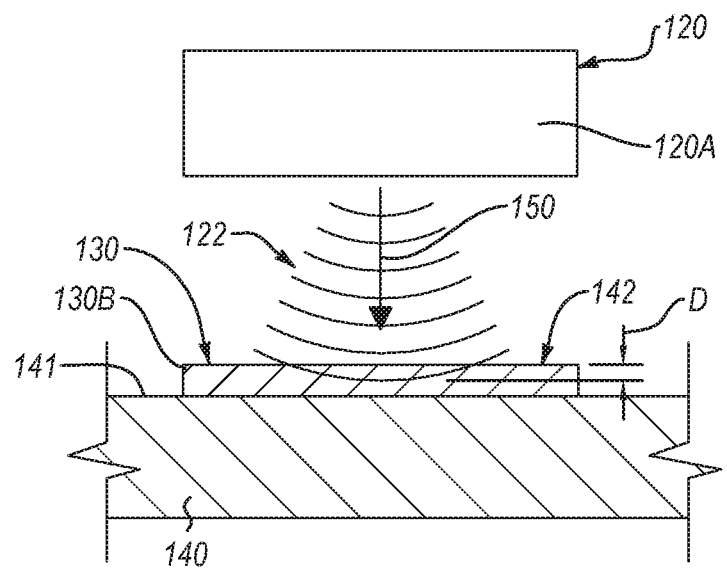
FIG. 3A is a schematic, cross-sectional, front view of a probe head of the system of FIG. 1, shown scanning a first layer of uncured fiber-reinforced polymeric material, according to one or more examples of the present disclosure.
Figure 3B:
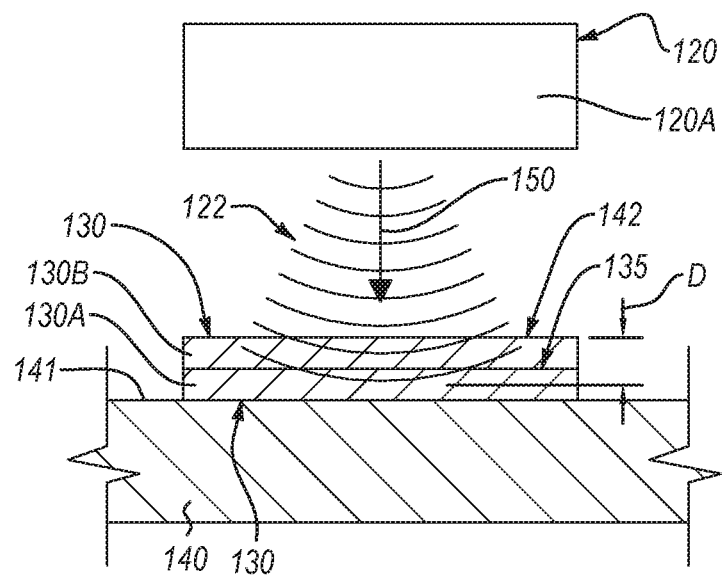
FIG. 3B is a schematic, cross-sectional, front view of a probe head of the system of FIG. 1, shown scanning a second layer of uncured fiber-reinforced polymeric material and an interface between the second layer and a first layer of uncured fiber-reinforced polymeric material, according to one or more examples of the present disclosure.
Figure 3C:
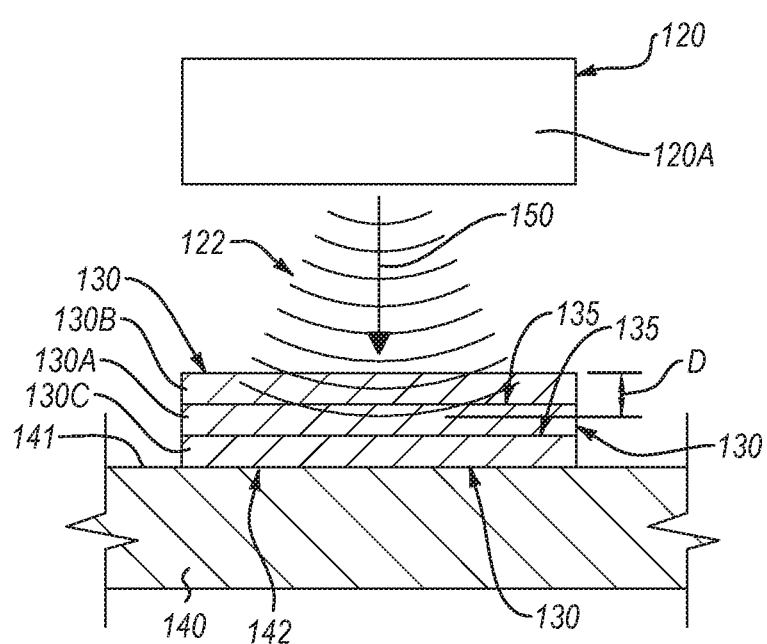
FIG. 3C is a schematic, cross-sectional, front view of a probe head of the system of FIG. 1, shown scanning a third layer of uncured fiber-reinforced polymeric material and an interface between the third layer and a second layer of uncured fiber-reinforced polymeric material, according to one or more examples of the present disclosure.

Referring to FIGS. 3A-3C, a step-by-step illustration of one example of depositing multiple tows 130 is shown. In FIG. 3A, the deposition head 110 has laid down a first one of the tows 130 directly onto the surface 141 of the object 140. Because no other tow 130 has been deposited onto the first tow 130 in FIG. 3A, the tow 130 in FIG. 3A is a most-recently deposited tow and thus a currently-applied tow 130B. Accordingly, as used herein, each tow 130 of the multiple tows 130 of a stacked configuration 142 is a currently-applied tow 130B when the tow 130 is a most-recently deposited tow of the multiple tows 130. A tow 130 is considered a most-recently deposited tow when the tow 130 is currently being deposited (e.g., only partially deposited) or is the most recently fully deposited tow, as long as no other tow has been at least partially deposited on the tow 130.

As shown in FIG. 3B, the deposition head 110 has laid down a second one of the tows 130 directly onto the first one of the tows 130. As the second one of the tows 130 is being laid down onto the first one of the tows 130, the first one of the tows 130, which was the currently-applied tow 130B, becomes a covered tow 130A and the second one of the tows 130 is considered the currently-applied tow 130B because it is the most-recently deposited tow. Accordingly, a tow 130 of the multiple tows 130 is a covered tow 130A when the tow 130 is directly covered by the currently-applied tow 130B (i.e., when the currently-applied tow 130B is deposited onto the tow 130). A stack interface 135 is defined between the currently-applied tow 130B and the covered tow 130A. The stack interface 135 becomes a bonding interface between the currently-applied tow 130B and the covered tow 130A when the stacked configuration 142 is cured. The covered tow 130A can also be considered a vertically-adjacent tow.

Now referring to FIG. 3C, the deposition head 110 has laid down a third one of the tows 130 directly onto the second one of the tows 130. As the third one of the tows 130 is being laid down onto the second one of the tows 130, the second one of the tows 130, which was the currently-applied tow 130B, becomes a covered tow 130A, the third one of the tows 130 is considered the currently-applied tow 130B because it is the most-recently deposited tow, and the first one of the tows 130, which was the covered tow 130A, is considered a previously-covered tow 130C. Another stack interface 135 is defined between the new currently-applied tow 130B and the new covered tow 130A.

If a desired number of layers of the stacked configuration 142 is more than three, the process depicted in FIGS. 3A-3C continues in a repetitive manner until a desired number of tows 130 are deposited in the stacked configuration 142. Of course, in certain examples, the stacked configuration 142 has less than three tows 130 forming the stacked configuration 142. In fact, in some examples, as used herein, a stacked configuration 142 can be formed of a single tow 130 defining a single layer of the stacked configuration 142.

Figure 4A:
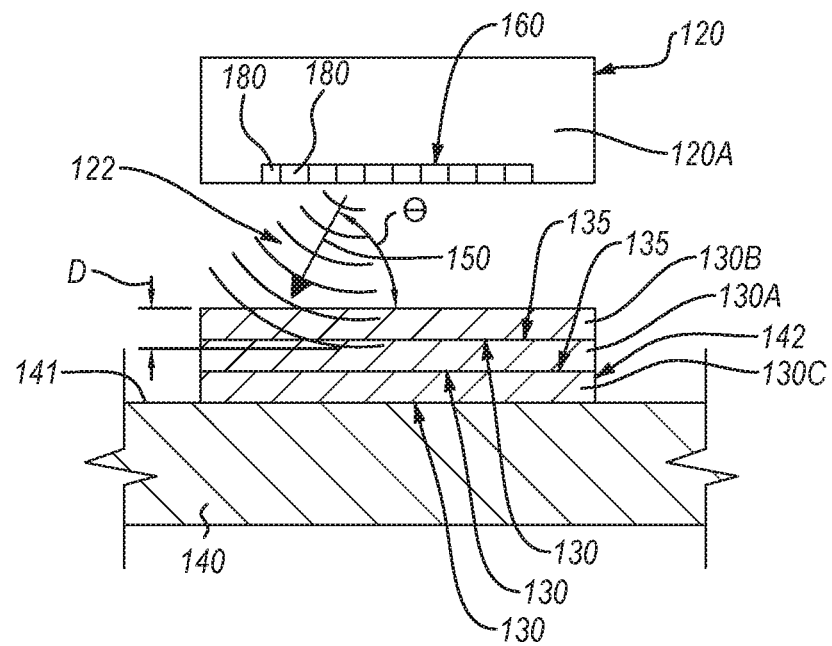
FIG. 4A is a schematic, cross-sectional, front view of a probe head of the system of FIG. 1, shown with a linear phased array of the probe head generating an incident microwave beam, according to one or more examples of the present disclosure.
Figure 4B:
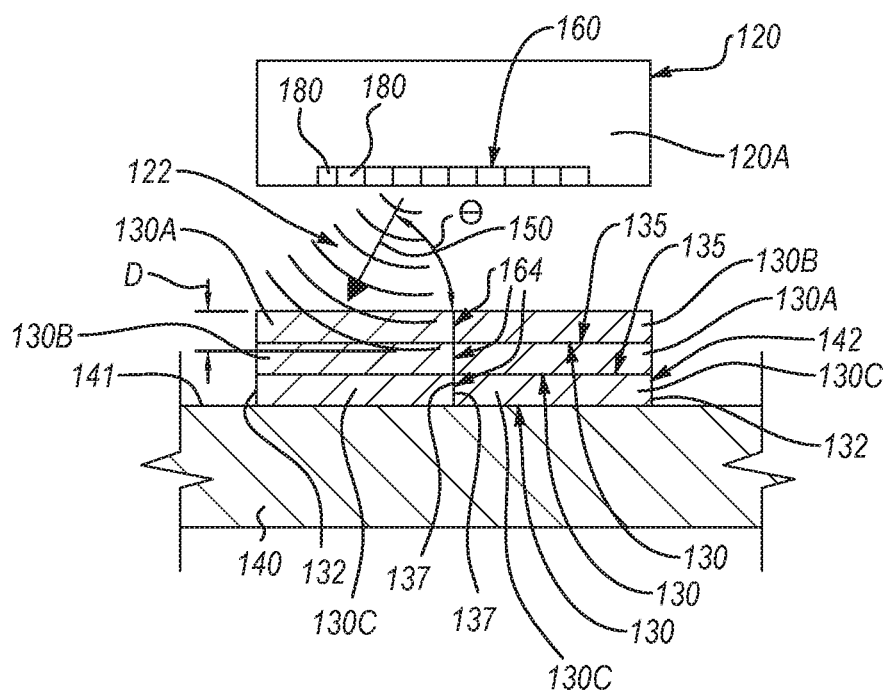
FIG. 4B is a schematic, cross-sectional, front view of a probe head of the system of FIG. 1, shown with a linear phased array of the probe head generating an incident microwave beam, according to one or more examples of the present disclosure.

Referring to FIG. 4B, when the deposition head 110 is configured to deposit multiple tows 130 at a time, such as shown in FIG. 2B, the process of laying down the tows 130 is similar to that depicted in FIGS. 3A-3C. However, instead of each layer of the stacked configuration 142 being defined by a single tow 130, each layer of the stacked configuration 142 is defined by two or more tows 130. Moreover, instead of the edges of the stacked configuration 142 being defined by the edges 132 (i.e., exterior edges) of the same currently-applied tow 130B (see, e.g., FIG. 4A), the edges of the stacked configuration 142 are defined by an exterior one of the edges 132 of one currently-applied tow 130B and an exterior one of the edges 132 of another currently-applied tow 130B forming the same layer of the stacked configuration (see, e.g., FIG. 4B).

After the stacked configuration 142 is completed, the stacked configuration 142 is formed into a part by curing the fiber-reinforced polymeric material. Curing the fiber-reinforced polymeric material involves heating the material up to at least a curing temperature of the material and, in some cases, applying a compressive force to the stacked configuration 142. Curing the polymeric material irreversibly hardens the polymeric material. Moreover, the polymeric material of each tow 130 forming the stacked configuration 142 bonds with the polymeric material of at least one adjacent tow 130 forming the stacked configuration 142 during the curing process such that all tows 130 of the stacked configuration 142 are bonded together after the curing process.

Prior to curing the fiber-reinforced polymeric material of the stacked configuration 142, the system 100 is configured to inspect each tow 130 of the stacked configuration 142 as the tow 130 is added to the stacked configuration 142 or before another tow 130 is deposited onto the tow 130. The inspection of the tows 130, as they are laid up prior to curing, helps to discover anomalies or imperfections in the fibers or the polymeric material of the tows, in the stack interfaces 135 between stacked ones of the tows 130, and the side interfaces 164 between side-by-side ones of the tows 130 before the tows 130 are cured. Such anomalies or imperfections that are discoverable or correctable in pre-cured tows 130 may not be discoverable or correctable after the tows 130 are cured.

The probe head 120 of the system 100 facilitates the inspection of each tow 130 of the stacked configuration 142 as the tow 130 is added to the stacked configuration 142 or before another tow 130 is deposited onto the tow 130. In some examples, the probe head 120 is configured to move along and be spatially offset from the currently-applied tow 130B after deposition of the currently-applied tow 130B. According to one example, to be spatially offset from the currently-applied tow 130B means to be out of physical contact with or physically separated from the currently-applied tow 130B. Moreover, in one example, as used herein, the currently-applied tow 130B is considered to be deposited when either any portion of the currently-applied tow 130B is deposited or all of the currently-applied tow 130B is deposited. However, the probe head 120 moves along and inspects deposited portions of the currently-applied tow 130B, rather than yet-to-be-deposited portions of the currently-applied tow 130B. For example, as shown in FIGS. 2A and 2B, the probe head 120 follows the applicator 117 of the deposition head 110 to be in position to inspect those portions of the currently-applied tow 130B as they are deposited by the applicator 117. As mentioned, the probe head 120 is co-movably fixed relative to the applicator 117, in some examples, such that a distance between the probe head 120 and the applicator 117 is fixed as the applicator 117 deposits the currently-applied tow 130B.

Referring to FIG. 2A, the probe head 120 includes a microwave sensor 120A that is configured to transmit an incident microwave beam 122 into the currently-applied tow 130B, in a beam direction 150, as the probe head 120 moves along the currently-applied tow 130B. Because the probe head 120 moves along and inspects deposited portions of the currently-applied tow 130, the incident microwave beam 122 is transmitted into a deposited portion of the currently-applied tow 130.

As described in more detail below, and referring to FIG. 8, the microwave sensor 120A of the probe head 120 is further configured to detect a reflected microwave beam 123 transmitted from the stacked configuration 142. The reflected microwave beam 123 includes at least a portion of the incident microwave beam 122 reflected from at least one of the currently-applied tow 130B or the stack interface 135 between the currently-applied tow 130B and the covered tow 130A. The characteristics of the reflected microwave beam 123 are analyzed to determine the presence of anomalies or imperfections in the currently-applied tow 130B, the stack interface 135, and/or the side interface 164. More specifically, in certain examples, the controller 108 is configured to determine a dielectric response of at least one of the currently-applied tow 130B or the stack interface 135 or the side interface 164 based on the characteristics of the reflected microwave beam 123. Certain determinable characteristics of the dielectric response are indicative of anomalies or imperfections in the currently-applied tow 130B, the stack interface 135, and/or the side interface 164. Using a microwave technique to inspect the uncured fiber-reinforced polymeric material is advantageous because the probe head 120 need not be in contact with the material under inspection, as is the case with other types of inspection, such as ultrasonic inspection. Accordingly, the uncured material can be inspected in a contactless manner, which helps alleviate contamination concerns.

The incident microwave beam 122 penetrates the stacked configuration 142 to a depth D that is dependent on the frequency of the incident microwave beam 122. As used herein, the depth D is the distance from the outermost facing surface of the stacked configuration 142, in a direction perpendicular to the outermost facing surface of the stacked configuration 142, to the location within the stacked configuration 142 associated with a maximum penetration of the incident microwave beam 122 into the stacked configuration 142. The outermost facing surface is the surface of the stacked configuration 142 that is closest to the probe head 120 when the probe head 120 is generating the incident microwave beam 122.

In some examples, the incident microwave beam 122 has a frequency low enough to pass entirely through the currently-applied tow 130B and high enough to pass entirely through no more than the currently-applied tow 130B and the stack interface 135 between the currently-applied tow 130B and the covered tow 130A. An incident microwave beam 122 with a frequency that is too low may penetrate too much of the stacked configuration 142 (e.g., depth D is too deep) such that the results of the analysis of the reflected microwave beam 123 would be inconclusive of any single layer of the stacked configuration 142. Moreover, should the frequency of the incident microwave beam 122 be too low, the beam may penetrate entirely through the stacked configuration 142 and reflect off the backside of the stacked configuration 142, which would result in erroneous data or false characteristics. Accordingly, for a stacked configuration 142 with at least two tows 130, the frequency of the incident microwave beam 122 is selected to penetrate the stacked configuration up to, at most, a depth D that extends beyond the stack interface 135, but not beyond the covered tow 130A. In this manner, the data obtained from the reflected microwave beam 123 is usable to provide conclusive results of just a single layer and/or a single stack interface of the stacked configuration 142.

However, when inspecting the first deposited tow(s) 130 or the tow(s) 130 deposited directly onto the surface 141 of the object 140, the frequency is selected such that the depth D does not penetrate beyond the first deposited tow(s) 130. Accordingly, in some examples, the controller 108 is configured to select a higher frequency for the incident microwave beam 122 when inspecting the first deposited tow(s) 130 compared to the frequency for inspecting subsequently deposited tows 130. Accordingly, the controller 108 can be configured to track the number of layers of tows 130 deposited onto the surface 141 of the object 140 and to adjust the frequency of the incident microwave beam 122 accordingly.

The desired depth D is also dependent on the thickness t of the tows 130, as well as the material properties of the tows 130. Accordingly, within examples, the frequency of the incident microwave beam 122 is selected based on the thickness t of the tows 130 and/or the material properties of the tows 130. For example, the thicker the tows 130, the lower the frequency of the incident microwave beam 122 needed to penetrate the stacked configuration to the desired depth D. Similarly, the denser the material of the tows 130, the lower the frequency of the incident microwave beam 122 needed to penetrate the stacked configuration to the desired depth D. Accordingly, based on known penetration depths of microwave beams of various frequencies into a fiber-reinforced polymeric material, the frequency of the incident microwave beam 122 can be selected. For example, in one type of fiber-reinforced polymeric material, a microwave beam with a frequency of 18.00 GHz penetrates 1.0 mm into a fiber-reinforced polymeric material and a microwave beam with a frequency of 12.73 GHz penetrates 1.5 mm into a fiber-reinforced polymeric material.

Generally, the frequency of the incident microwave beam 122 is considerably higher than those used in conventional microwave inspection techniques. In one example, the frequency of the incident microwave beam 122 is at least 15 GHz. According to some examples, the frequency of the incident microwave beam 122 is between 15 GHz and 25 GHz, inclusive. In other examples, the frequency of the incident microwave beam 122 is between 25 GHz and 50 GHz, inclusive. In other examples, the frequency of the incident microwave beam 122 is between 50 GHz and 100 GHz, inclusive.

Figure 8:
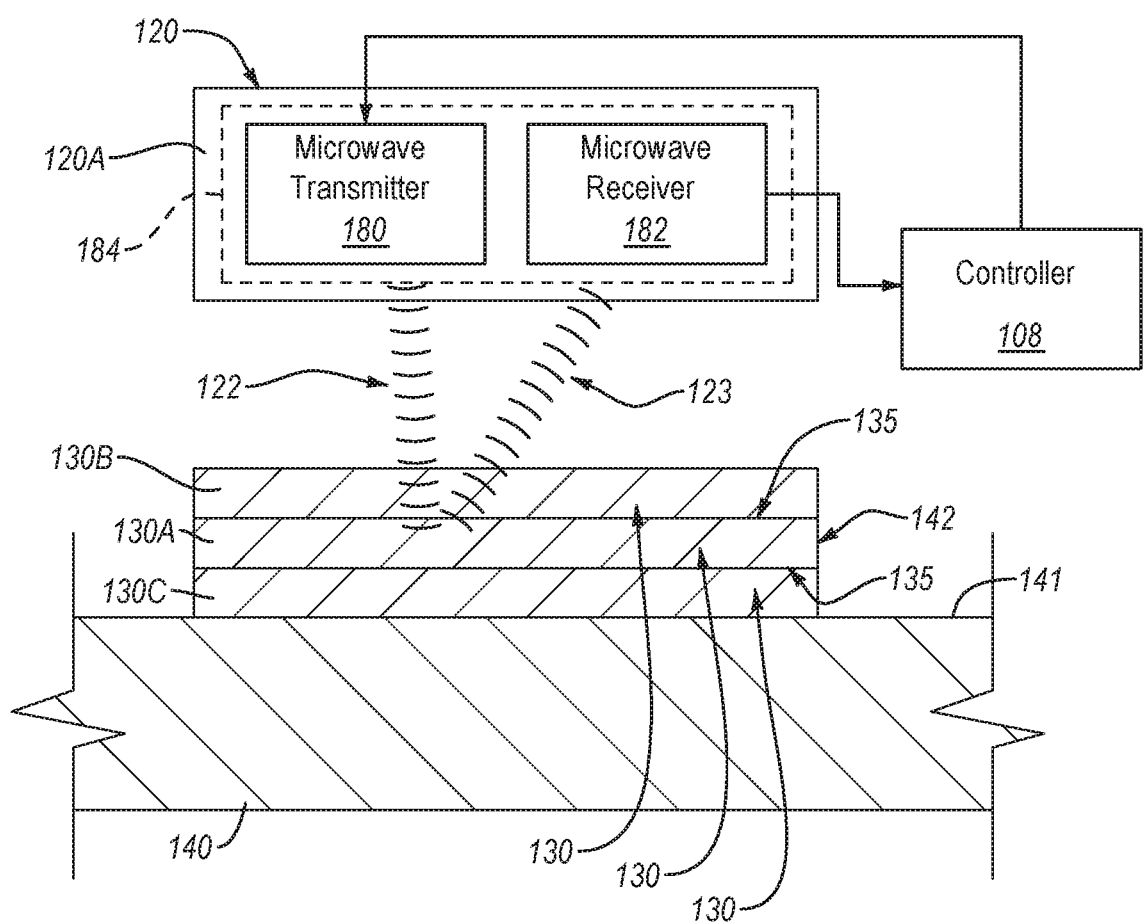
FIG. 8 is a schematic, cross-sectional, front view of a probe head and a controller of the system of FIG. 1, according to one or more examples of the present disclosure.

Referring to FIG. 8, in some examples, the microwave sensor 120A of the probe head 120 includes a microwave transmitter 180 and a microwave receiver 182. The microwave transmitter 180 is configured to generate the incident microwave beam 122 and transmit the incident microwave beam 122 into the currently-applied tow 130B and, in some examples, the stack interface 135 and/or the side interface 164. The microwave receiver 182 is configured to receive the reflected microwave beam 123 from the stacked configuration 142 and communicate data concerning the reflected microwave beam 123 to a controller 108 of the system 100. The data can include characteristics of the reflected microwave beam 123. The controller 108 is configured to determine the presence of anomalies or imperfections in the currently-applied tow 130B and, in some examples, the stack interface 135 and/or the side interface 164 based on a comparison between the data concerning the reflected microwave beam 123 and the known characteristics of the incident microwave beam 122. For example, knowing the characteristics of the incidence microwave beam 122, and assuming no anomalies or imperfections, the reflected microwave beam 123 should have certain expected characteristics. When the actual characteristics of the reflected microwave beam 123, obtained from the data gathered and transmitted by the microwave receiver 182, differ from the expected characteristics, then the controller 108 is able to determine that anomalies or imperfections are present.

In some examples, the microwave transmitter 180 and the microwave receiver 182 are physically separate devices, such as one or more transducers each specifically adapted to transmit microwaves and one or more transducers each specifically adapted to receive microwaves. However, according to certain examples, the microwave transmitter 180 and the microwave receiver 182 are combined into a single device, such as a microwave transceiver 184. The microwave sensor 120A includes one or more microwave transceivers 184 each specifically adapted to both transmit microwaves and receive microwaves.

Referring to FIG. 4A, in some examples, the microwave sensor 120A of the probe head 120 includes a linear phased array 160 of microwave transmitters 180. The microwave transmitters 180 are integrated into microwave transceivers 184 in some examples. Each one of the microwave transmitters 180 (or microwave transceivers 184) generates a microwave signal. The incident microwave beam 122 includes a combination of the microwave signals generated by the linear phased array 160 of microwave transmitters 180 (or microwave transceivers 184). In some examples, the linear phased array 160 is configured to phase shift the generation of the microwave signals. Phase shifting the generation of the microwave signals involves progressively delaying the generation of microwave signals going up the line of microwave transmitters 180 of the linear phased array 160. The progressive delaying of the microwave signals results in the microwave signals constructively combining to form the incident microwave beam 122 as a plane wave. In some examples, the linear phased array 160 includes various electrical circuits, such as phase shifters that each control the feed current supplied to a corresponding one of the microwave transmitters 180. The phase shifters are selectively controlled by the controller 108 to change the phase shift of the generation of the microwave signals.

The beam direction 150 of the transmission of the incident microwave beam 122, which is defined by an angle θ relative to the currently-applied tow 130B at the inspection site, is dependent on the phase shifts of the microwave signals. In other words, the phase shifts or timing of the generation of the microwave signals can change the direction of the transmission of the incident microwave beam 122. By changing the phase shift or timing, the beam direction 150 of the incident microwave beam 122, or angle θ, can be adjusted. The selective adjustment allows the incident microwave beam 122 to be rastered or moved laterally across the width W of the currently-applied tow 130B (or the widths W of multiple side-by-side currently-applied tows 130B, in a first lateral direction 124 or a second lateral direction 126 substantially perpendicular to the movement of the probe head 120, as shown in FIGS. 2A and 2B.

Rastering the incident microwave beam 122 promotes a compact probe head 120 because the linear phased array 160 can be smaller relative to the size of the tow 130 or tows 130 being inspected. Moreover, a compact probe head 120 facilitates the direct coupling of the probe head 120 to the deposition head 110, which promotes inspection of the tows 130 as they are being deposited or between applications of successive layers.

In some examples, as shown in FIG. 1, the probe head 120 is coupled to the same robot 102 to which the deposition head 110 is coupled. According to certain examples, the probe head 120 is affixed directly to, or integrated into, the deposition head 110. When coupled to the same robot 102 or directly affixed to the deposition head 110, the probe head 120 is movable along the currently-applied tow 130B along with the deposition head 110 via operation of the robot 102.

Figure 7:
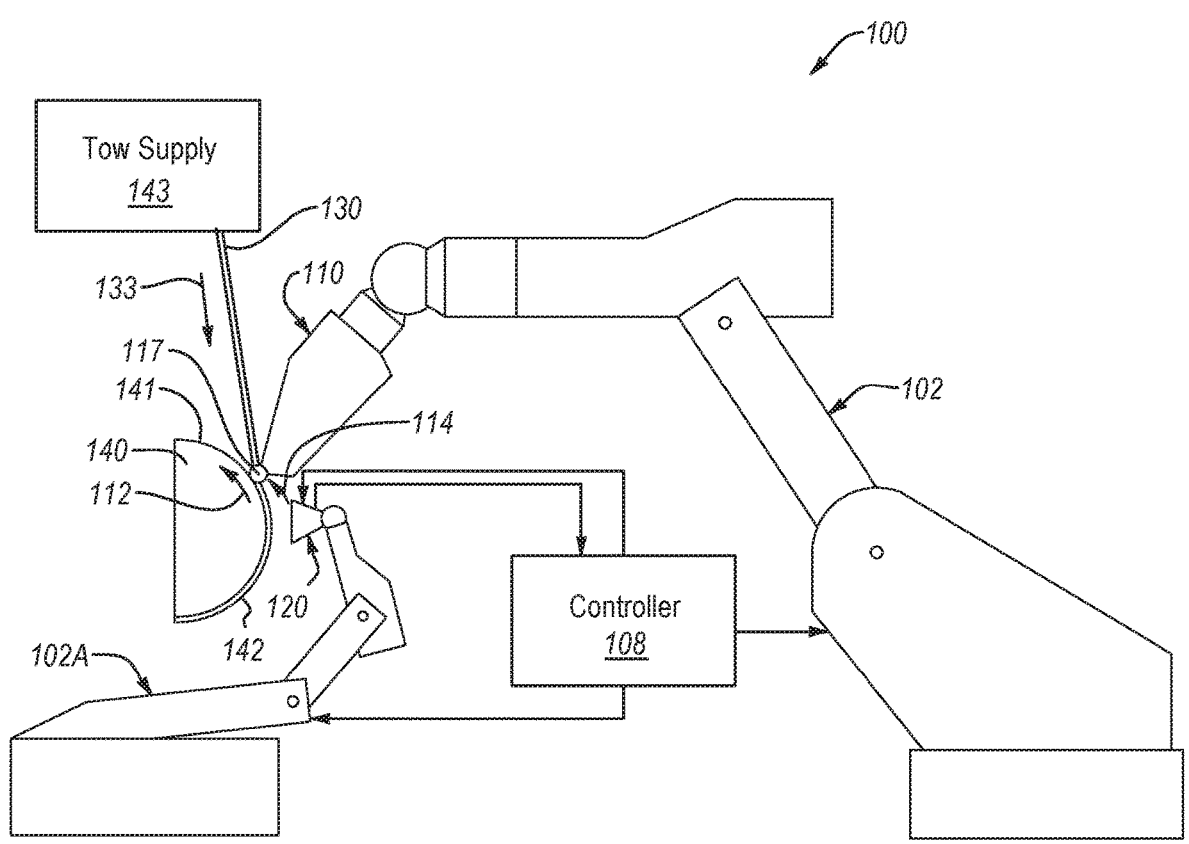
FIG. 7 is a schematic, elevation view of a system for depositing multiple tows of uncured fiber-reinforced polymeric material one layer at a time and inspecting the multiple tows one layer at a time, according to one or more examples of the present disclosure.

According to alternative examples, as shown in FIG. 7, the system 100 further includes a second robot 102A. The second robot 102A is independently movable and controllable relative to the robot 102. In such examples, the deposition head 110 is coupled to the robot 102 and movable by the robot 102 along the deposition path 112 to deposit the multiple tows 130 in the stacked configuration 142. In contrast, the probe head 120 is coupled to the second robot 102A and movable by the second robot 102A in an inspection path 114 along the currently-applied tow 130B independently of the deposition head 110. In some examples, the second robot 102A moves the probe head 120 in the inspection path 114 along the currently-applied tow 130B at the same rate as and at the same distance from the deposition head 110. According to other examples, the second robot 102A move the probe head 120 in the inspection path 114 along the currently-applied tow 130B at a different rate or after the deposition head 110 has completed the deposition of the entire currently-applied tow 130B.

Figure 5:
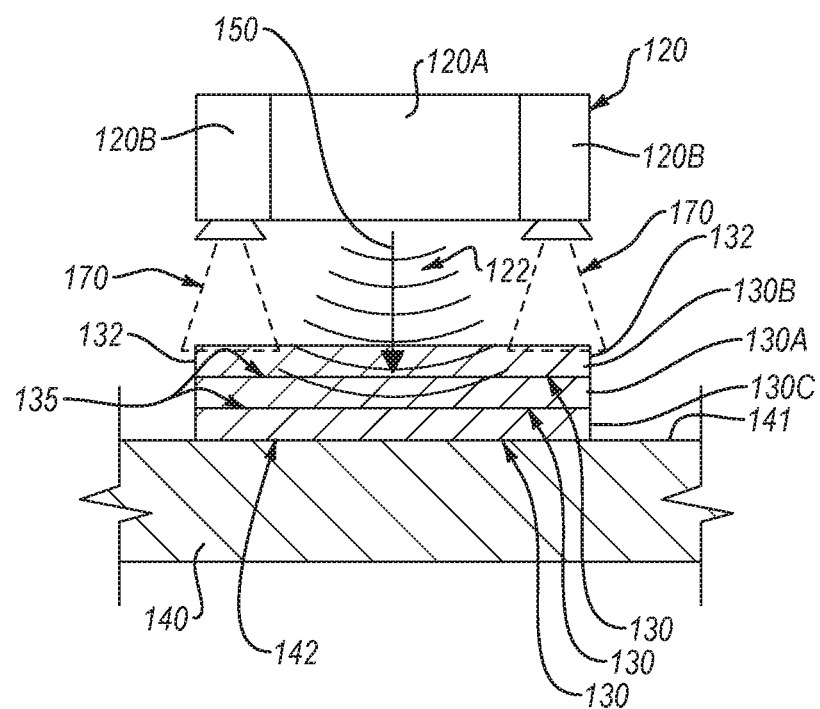
FIG. 5 is a schematic, cross-sectional, front view of a probe head of the system of FIG. 1 having a microwave sensor and edge detectors, according to one or more examples of the present disclosure.

In some examples, the incident microwave beam 122 is rastered up to, but not beyond, the edges 132 of the currently-applied tow 130B (see, e.g., FIG. 5). Directing a portion of the incident microwave beam 122 beyond the edges 132 results in an erroneous inspection (e.g., false positives) because the portion is not reflected back to the probe head 120. When inspecting parts with large surface areas, some conventional techniques do not experience such edge effects due to the shear size of the surface area. However, when inspecting features have smaller surface areas, such as the tows 130, conventional techniques are not equipped to account for or mitigate edge effects.

To help prevent erroneous inspection due to edge effects, as shown in FIG. 5, certain examples of the probe head 120 include at least one edge detector 120B. The probe head 120 of FIG. 5 includes two edge detectors 120B, each configured to detect a corresponding one of two edges 132 of each layer of the stacked configuration 142. The edge detectors 120B flank the microwave sensor 120A, such that the microwave sensor 120A is between the edge detectors 120B. In some examples, the probe head 120 includes one edge detector 120B that is configured to detect both of the two edges 132 of each layer. As described above, the edges 132 of each layer can be the edges 132 of a single tow 130, when the deposition head 110 deposits one tow 130 at a time, or one edge 132 of one tow 130 and one edge 132 of another tow 130, when the deposition head 110 deposits multiple tows 130 at a time in a side-by-side arrangement.

In the illustrated example, the edge detector 120B includes a camera that is configured to capture images of one or both of the edges 132 based on visible light 170 reflected from the edge or edges of the currently-applied tow 130B. The images are processed by the controller 108 to detect the location of the edge 132 or edges 132. In certain examples, the image processing technique utilized by the controller 108 to detect the location of the edge 132 or edges 132 is one or more of a canny edge detection technique, a sobel edge detection technique, or a sobel-canny edge detection technique. According to alternative examples, the edge detector 120B includes a line scan or line laser that utilizes optical triangulation to detect the location of the edge 132 or edges 132. The detected location of the edges 132 is utilized by controller 108 to control the lateral movement of the incident microwave beam 122 by the linear phased array 160 to limit the movement to between the edges 132. In other words, the probe head 120 is controllable by the controller 108 to prevent movement of the incident microwave beam 122 beyond the edges 132 (e.g., configured to limit movement of the incident microwave beam 122 beyond the at least one edge(s) 132) in response to the detected location of the edge(s) 132.

In some examples, to enable multi-modal inspection of the currently-applied tows 130B of the stacked configuration 142, the probe head 120 includes additional inspection devices that supplement the inspection capabilities of the microwave sensor 120A. According to one example, shown in FIG. 6, the probe head 120 additionally includes an infrared camera 120C. The infrared camera 120C is configured to generate a thermal image of the currently-applied tow 130B based on infrared radiation 172 from the currently-applied tow 130B. The thermal excitation of the currently-applied tow 130B that is captured by the infrared camera 120C is generated by the application of heat to the currently-applied tow 130B. In certain examples, the heat is applied to the currently-applied tow 130B from the deposition head 110, which generates heat, as the deposition head 110 deposits the currently-applied tow 130B. Additionally, or alternatively, in some examples, heat is applied to the currently-applied tow 130B from an external heat source, such as a hot air source or a heat lamp.

From the thermal image, the controller 108 is enabled to determine surface and sub-surface characteristics (e.g., anomalies and imperfections) of the currently-applied tow 130B, the stack interface 135, and/or the side interface 164. The surface and sub-surface characteristics determined from the thermal image captured by the infrared camera 120C are compared with those determined by the microwave sensor 120A to provide a more complete analysis of the presence of anomalies and imperfections in the currently-applied tow 130B, the stack interface 135, and/or the side interface 164. For example, the controller 108 can be configured to fuse together the characteristics determined from the infrared camera 120C and the microwave sensor 120A into a composite image from which further insights into the anomalies and imperfections in the currently-applied tow 130B, the stack interface 135, and/or the side interface 164 can be obtained.

Figure 6:
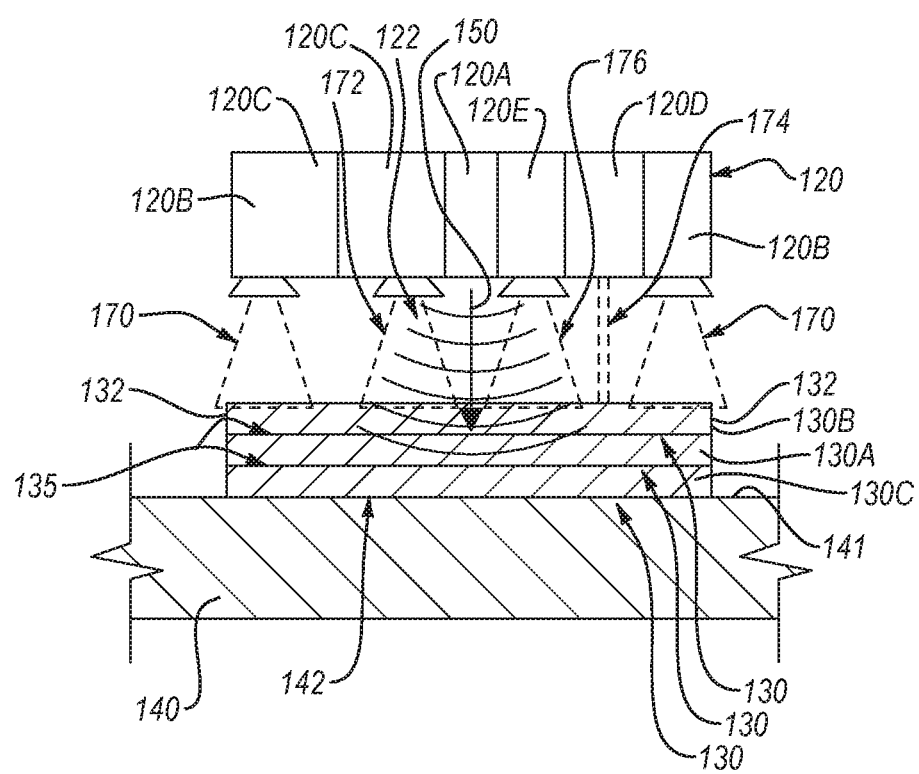
FIG. 6 is a schematic, cross-sectional, front view of a probe head of the system of FIG. 1 having a microwave sensor, edge detectors, an infrared camera, a laser profilometer, and a visual camera, according to one or more examples of the present disclosure.

According to another example, shown in FIG. 6, in addition or alternative to the infrared camera 120C, the probe head 120 includes a laser profilometer 120D. The laser profilometer 120D is configured to transmit a laser beam 174 to the currently-applied tow 130B and determine profile characteristics of the currently-applied tow 130B based on a displacement of the laser beam 174 after impacting the currently-applied tow 130B. From the profile characteristics, the controller 108 is enabled to determine surface characteristics (e.g., anomalies and imperfections) of the currently-applied tow 130B. The surface characteristics determined by the laser profilometer 120D are compared with those determined by the microwave sensor 120A (and optionally the infrared camera 120C) to provide a more complete analysis of the presence of anomalies and imperfections in the currently-applied tow 130B, the stack interface 135, and/or the side interface 164. For example, the controller 108 can be configured to fuse together the characteristics determined from the infrared camera 120C, the laser profilometer 120D, and/or the microwave sensor 120A into a composite image from which further insights into the anomalies and imperfections in the currently-applied tow 130B, the stack interface 135, and/or the side interface 164 can be obtained.

In yet another example, shown in FIG. 6, in addition or alternative to the infrared camera 120C and/or the laser profilometer 120D, the probe head 120 includes a visual camera 120E. The visual camera 120E is configured to generate a visual image of the currently-applied tow 130B based on visible light 176 reflected from the currently-applied tow 130B. The controller 108 is configured to determine surface characteristics (e.g., anomalies and imperfections) of the currently-applied tow 130B based on the visual image generated by the visual camera 120E. The surface characteristics obtained from the visual camera 120E are compared with those determined by the microwave sensor 120A (and optionally the infrared camera 120C and the laser profilometer 120D) to provide a more complete analysis of the presence of anomalies and imperfections in the currently-applied tow 130B, the stack interface 135, and/or the side interface 164. For example, the controller 108 can be configured to fuse together the characteristics determined from the infrared camera 120C, the laser profilometer 120D, the visual camera 120E, and/or the microwave sensor 120A into a composite image from which further insights into the anomalies and imperfections in the currently-applied tow 130B, the stack interface 135, and/or the side interface 164 can be obtained.

In some examples, the probe head 120 includes all of the microwave sensor 120A, the edge detector 120B, the infrared camera 120C, the laser profilometer 120D, and the visual camera 120E. However, in other examples, the probe head 120 includes the microwave sensor 120A and some, but not all, of the edge detector 120B, the infrared camera 120C, the laser profilometer 120D, and the visual camera 120E. In yet other examples, the probe head 120 includes the microwave sensor 120A and one other of the edge detector 120B, the infrared camera 120C, the laser profilometer 120D, and the visual camera 120E. Of course, as described above, in certain examples, the probe head 120 includes the microwave sensor 120A and none of the edge detector 120B, the infrared camera 120C, the laser profilometer 120D, and the visual camera 120E.

Figure 9:
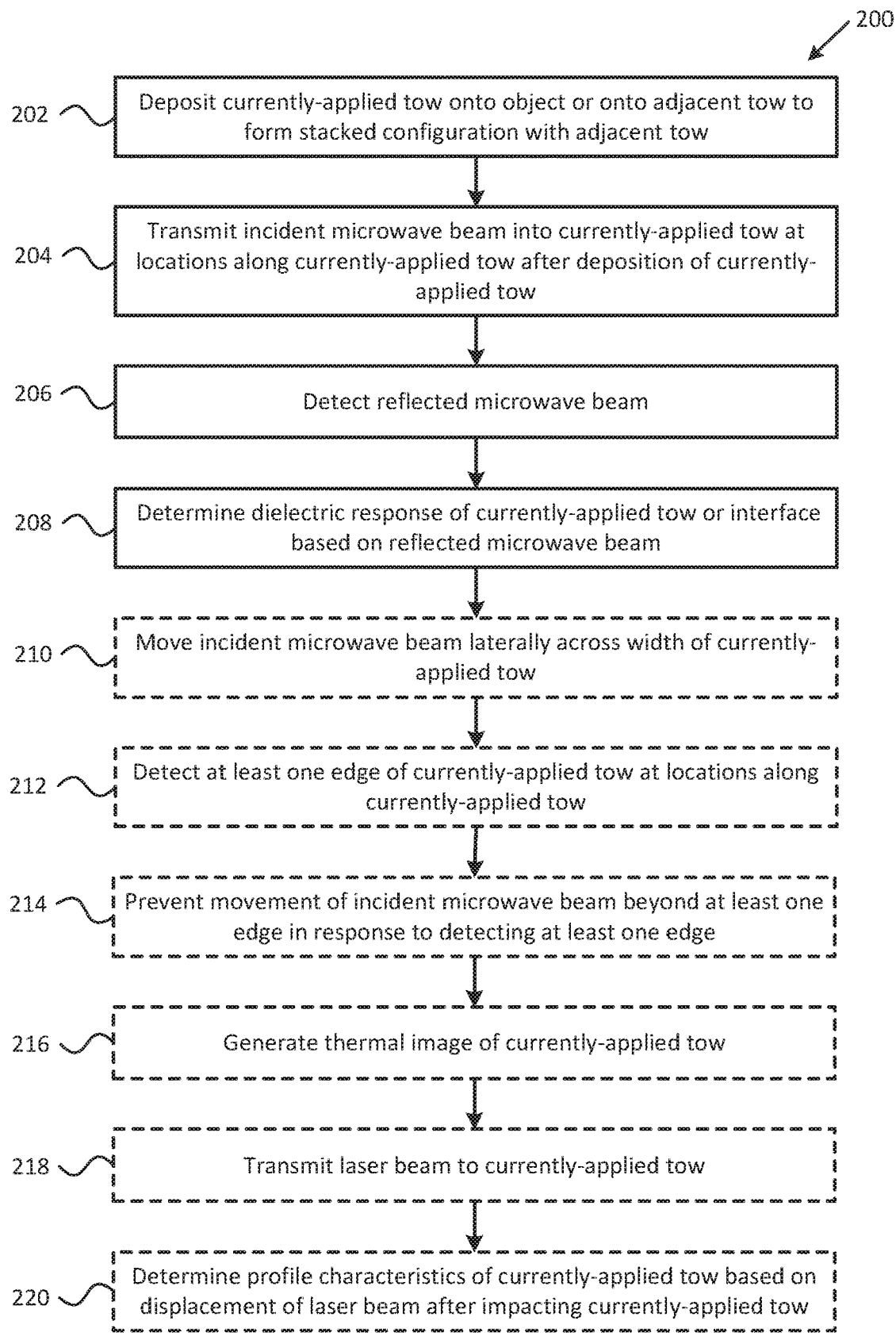
FIG. 9 is a schematic flow diagram of a method of depositing multiple tows of uncured fiber-reinforced polymeric material one layer at a time and inspecting the multiple tows one layer at a time, according to one or more examples of the present disclosure.

Referring to FIG. 9, according to one example, a method 200 of depositing multiple tows 130 of uncured fiber-reinforced polymeric material one layer at a time and inspecting the multiple tows 130 one layer at a time, using the system 100, is disclosed. The method 200 includes (block 202) depositing the currently-applied tow 130B onto the object or onto a covered tow 130A, if a currently-applied tow 130B was previously applied, to form a layer of a stacked configuration 142. Moreover, if the currently-applied tow 130B is deposited onto the covered tow 130A, the combination of the currently-applied tow 130B and the covered tow 130A form the stacked configuration 142. In contrast, if the currently-applied tow 130B is deposited onto the object 140, then the currently-applied tow 130B does not yet form part of a stacked configuration 142 because a stacked configuration 142 is not formed until two or more tows 130 are stacked together. In some examples, block 202 further includes depositing at least two currently-applied tows 130B onto the object or onto at least two covered tows 130A such that the at least two currently-applied tows 130B together form a layer of a stacked configuration 142.

The method 200 further includes (block 204) transmitting the incident microwave beam 122 into the currently-applied tow 130B at locations along the currently-applied tow 130B after deposition of the currently-applied tow 130B. The incident microwave beam 122 has a frequency low enough to pass entirely through the currently-applied tow 130B and high enough to pass entirely through no more than the currently-applied tow 130B and a stack interface 135 between the currently-applied tow 130B and the covered tow 130A. In some examples, the step of depositing the currently-applied tow 130B at block 202 and the step of transmitting the incident microwave beam 122 into the currently-applied tow 130B at block 204 are performed concurrently.

The method 200 also includes (block 206) detecting the reflected microwave beam 123 and (block 208) determining a dielectric response of the currently-applied tow 130B or the stack interface 135 based on the reflected microwave beam 123. In some examples, which include layers of laterally-adjacent tows 130 in a side-by-side configuration, block 208 includes determining the dielectric response of the side interface 164 between laterally-adjacent tows 130.

According to some examples, the method 200 additionally includes (block 210) moving the incident microwave beam 122 laterally across the width of the currently-applied tow 130B or widths of the currently-applied tows 130B. The method 200 also includes, in certain examples, (block 212) detecting one edge 132 or both edges 132 of the currently-applied tow 130B at the locations along the currently-applied tow 30B. The method 200 further includes, in some examples, (block 214) preventing movement of the incident microwave beam 122 beyond the edge(s) 132 in response to detecting the edge(s) 132.

In some examples, the method 200 additionally includes (block 216) generating the thermal image of the currently-applied tow 130B concurrently with the step of depositing the currently-applied tow 130B at block 202 and the step of transmitting the incident microwave beam 122 into the currently-applied tow 130B at block 204. Alternatively, or additionally, the method 200 includes (block 218) transmitting the laser beam 174 to the currently-applied tow 130B concurrently with the step of depositing the currently-applied tow 130B at block 202 and the step of transmitting the incident microwave beam 122 into the currently-applied tow 130B at block 204, and (block 220) determining profile characteristics of the currently-applied tow 130B based on a displacement of the laser beam 174 after impacting the currently-applied tow 130B.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The schematic flow chart diagrams included herein are generally set forth as logical flow chart diagrams. As such, the depicted order and labeled steps are indicative of one example of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The controller 108, which is an electronic controller, described in this specification may be implemented as a hardware circuit comprising custom VLSI circuits or gate arrays, off-the-shelf semiconductors such as logic chips, transistors, or other discrete components. The controller may also be implemented in programmable hardware devices such as field programmable gate arrays, programmable array logic, programmable logic devices or the like.

The controller may also be implemented in code and/or software for execution by various types of processors. An identified module of code may, for instance, comprise one or more physical or logical blocks of executable code which may, for instance, be organized as an object, procedure, or function. Nevertheless, the executables of the controller need not be physically located together, but may comprise disparate instructions stored in different locations which, when joined logically together, comprise the controller and achieve the stated purpose for the controller.

Indeed, code of the controller may be a single instruction, or many instructions, and may even be distributed over several different code segments, among different programs, and across several memory devices. Similarly, operational data may be identified and illustrated herein within the controller, and may be embodied in any suitable form and organized within any suitable type of data structure. The operational data may be collected as a single data set, or may be distributed over different locations including over different computer readable storage devices. Where the controller or portions of the controller are implemented in software, the software portions are stored on one or more computer readable storage devices.

Any combination of one or more computer readable medium may be utilized. The computer readable medium may be a computer readable storage medium. The computer readable storage medium may be a storage device storing the code. The storage device may be, for example, but not limited to, an electronic, magnetic, optical, electromagnetic, infrared, holographic, micromechanical, or semiconductor system, apparatus, or device, or any suitable combination of the foregoing.

More specific examples (a non-exhaustive list) of the storage device would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Code for carrying out operations for embodiments may be written in any combination of one or more programming languages including an object oriented programming language such as Python, Ruby, Java, Smalltalk, C++, or the like, and conventional procedural programming languages, such as the "C" programming language, or the like, and/or machine languages such as assembly languages. The code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The described features, structures, or characteristics of the embodiments may be combined in any suitable manner. In the above description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Aspects of the embodiments are described below with reference to schematic flowchart diagrams and/or schematic block diagrams of methods, apparatuses, systems, and program products according to embodiments. It will be understood that each block of the schematic flowchart diagrams and/or schematic block diagrams, and combinations of blocks in the schematic flowchart diagrams and/or schematic block diagrams, can be implemented by code. These code may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The code may also be stored in a storage device that can direct a computer, other programmable data processing apparatus, or other devices to function in a particular manner, such that the instructions stored in the storage device produce an article of manufacture including instructions which implement the function/act specified in the schematic flowchart diagrams and/or schematic block diagrams block or blocks.

The code may also be loaded onto a computer, other programmable data processing apparatus, or other devices to cause a series of operational steps to be performed on the computer, other programmable apparatus or other devices to produce a computer implemented process such that the code which execute on the computer or other programmable apparatus provide processes for implementing the functions/acts specified in the flowchart and/or block diagram block or blocks.

The present subject matter may be embodied in other specific forms without departing from its spirit or essential characteristics. The described examples are to be considered in all respects only as illustrative and not restrictive. All changes which come within the meaning and range of equivalency of the claims are to be embraced within their scope.

What is claimed is:

1. A system, comprising:
a deposition head, configured to deposit multiple tows of uncured fiber-reinforced polymeric material in a stacked configuration one layer at a time, wherein each tow of the multiple tows is a currently-applied tow when the tow is a most-recently deposited tow of the multiple tows and a tow of the multiple tows is a covered tow when the tow is directly covered by the currently-applied tow; and
a probe head, configured to move along and be spatially offset from the currently-applied tow after deposition of the currently-applied tow, wherein:
the probe head is further configured to transmit an incident microwave beam into the currently-applied tow as the probe head moves along the currently-applied tow; and
the incident microwave beam has a frequency low enough to pass entirely through the currently-applied tow and high enough to pass entirely through no more than the currently-applied tow and the covered tow.

2. The system according to claim 1, wherein the frequency of the incident microwave beam is between 50 GHz and 100 GHz.

3. The system according to claim 1, wherein the frequency of the incident microwave beam is high enough to pass entirely through no more than the currently-applied tow and a stack interface between the currently-applied tow and the covered tow.

4. The system according to claim 1, wherein:
the probe head comprises a linear phased array of microwave transmitters;
each one of the microwave transmitters generates a microwave signal;
the incident microwave beam comprises a combination of the microwave signals generated by the linear phased array of microwave transmitters;
the linear phased array is configured to phase shift the generation of the microwave signals; and
the probe head is configured to move the incident microwave beam laterally across a width of the currently-applied tow, in a direction substantially perpendicular to movement of the probe head along the currently-applied tow, by selectively controlling the linear phased array to change the phase shift of the generation of the microwave signals.

5. The system according to claim 4, wherein:
the probe head further comprises at least one edge detector, which is configured to detect at least one edge of the currently-applied tow as the probe head moves along the currently-applied tow; and
the probe head is further configured to prevent movement of the incident microwave beam beyond the at least one edge in response to detection of the at least one edge of the currently-applied tow.

6. The system according to claim 5, wherein:
the deposition head is further configured to deposit multiple tows of uncured fiber-reinforced polymeric material in a side-by-side arrangement one layer at a time;
the stacked configuration further comprises multiple layers of tows in the side-by-side arrangement;
the at least one edge detector is further configured to detect the edge of one currently-applied tow, of a currently-applied layer of tows in the side-by-side arrangement, and the edge of another currently-applied tow, of the currently-applied layer of tows in the side-by-side arrangement; and
the probe head is further configured to prevent movement of the incident microwave beam beyond the one edge of the one currently-applied tow, of the currently-applied layer of tows in the side-by-side arrangement, and the edge of the other currently-applied tow, of the currently-applied layer of tows in the side-by-side arrangement, in response to detection of the edge of the one currently-applied tow, of the currently-applied layer of tows in the side-by-side arrangement, and the edge of the other currently-applied tow, of the currently-applied layer of tows in the side-by-side arrangement.

7. The system according to claim 1, wherein the probe head further comprises a laser profilometer configured to:
transmit a laser beam to the currently-applied tow; and
determine profile characteristics of the currently-applied tow based on a displacement of the laser beam after impacting the currently-applied tow.

8. The system according to claim 1, wherein:
the deposition head moves along a deposition path to deposit the multiple tows of uncured fiber-reinforced polymeric material in the stacked configuration; and
the probe head is non-movably affixed to the deposition head such that the probe head moves along the deposition path with the deposition head.

9. The system according to claim 1, further comprising a robot, wherein:
the deposition head is coupled to the robot such that the deposition head is movable, to deposit the multiple tows in the stacked configuration, by the robot; and
the probe head is coupled to the robot such that the probe head is movable, along each tow of the of the multiple tows, by the robot.

10. The system according to claim 1, further comprising:
a robot; and
a second robot, which is independently movable relative to the robot; wherein:
the deposition head is coupled to the robot such that the deposition head is movable, to deposit the multiple tows in the stacked configuration, by the robot; and
the probe head is coupled to the second robot such that the probe head is movable, along each tow of the of the multiple tows, by the second robot.

11. The system according to claim 1, wherein:
the probe head is further configured to detect a reflected microwave beam; and
the reflected microwave beam comprises at least a portion of the incident microwave beam reflected from at least one of:
the currently-applied tow; or
a stack interface between the currently-applied tow and the covered tow.

12. The system according to claim 11, further comprising a controller configured to determine a dielectric response of at least one of the currently-applied tow or the stack interface based on the reflected microwave beam.

13. The system according to claim 1, wherein the probe head further comprises at least one of:
an infrared camera configured to generate a thermal image of the currently-applied tow based on infrared radiation from the currently-applied tow; or
a visual camera configured to generate a visual image of the currently-applied tow.

14. A probe head, comprising:
a microwave sensor, configured to transmit an incident microwave beam into a currently-applied tow, forming part of a stacked configuration of multiple tows of uncured fiber-reinforced polymeric material, as the microwave sensor moves along the currently-applied tow, wherein:
the incident microwave beam has a frequency low enough to pass entirely through currently-applied tow and high enough to pass entirely through no more than the currently-applied tow and a covered tow on which the currently-applied tow is directly stacked;
the microwave sensor further comprises a linear phased array of microwave transmitters;
each one of the microwave transmitters generates a microwave signal;
the incident microwave beam comprises a combination of the microwave signals generated by the linear phased array of microwave transmitters;
the linear phased array is configured to phase shift the generation of the microwave signals; and
the microwave sensor is configured to move the incident microwave beam laterally across a width of the currently-applied tow, in a direction perpendicular to movement of the probe head along the currently-applied tow, by selectively controlling the linear phased array to change the phase shift of the generation of the microwave signals; and at least one edge detector, configured to detect at least one edge of the currently-applied tow as the at least one edge detector moves along the currently-applied tow, wherein the microwave sensor is further configured to limit movement of the incident microwave beam beyond the at least one edge in response to detection of the at least one edge of the currently-applied tow.

15. The probe head according to claim 14, further comprising at least one of:
an infrared camera configured to generate a thermal image of the currently-applied tow based on infrared radiation from the currently-applied tow; or
a laser profilometer configured to:
transmit a laser beam to the currently-applied tow; and
determine profile characteristics of the currently-applied tow based on a displacement of the laser beam upon impacting the currently-applied tow.

16. A method, comprising:
depositing a currently-applied tow, made of uncured fiber-reinforced polymeric material, onto an object or onto a covered tow to form a stacked configuration with the covered tow;
transmitting an incident microwave beam into the currently-applied tow at locations along the currently-applied tow after deposition of the currently-applied tow, wherein the incident microwave beam has a frequency low enough to pass entirely through the currently-applied tow and high enough to pass entirely through no more than the currently-applied tow and a stack interface between the currently-applied tow and the covered tow;
detecting a reflected microwave beam, comprising at least a portion of the incident microwave beam reflected from at least one of the currently-applied tow or the stack interface; and
determining a dielectric response of the currently-applied tow or the stack interface based on the reflected microwave beam.

17. The method according to claim 16, further comprising:
moving the incident microwave beam laterally across a width of the currently-applied tow;
detecting at least one edge of the currently-applied tow at the locations along the currently-applied tow; and
preventing movement of the incident microwave beam beyond the at least one edge in response to detecting the at least one edge.

18. The method according to claim 16, wherein the step of depositing the currently-applied tow and the step of transmitting the incident microwave beam into the currently-applied tow are performed concurrently.

19. The method according to claim 18, further comprising generating a thermal image of the currently-applied tow concurrently with the step of depositing the currently-applied tow and the step of transmitting the incident microwave beam into the currently-applied tow, wherein the thermal image of the currently-applied tow is based on infrared radiation from the currently-applied tow.

20. The method according to claim 18, further comprising:
transmitting a laser beam to the currently-applied tow concurrently with the step of depositing the currently-applied tow and the step of transmitting the incident microwave beam into the currently-applied tow; and determining profile characteristics of the currently-applied tow based on a displacement of the laser beam after impacting the currently-applied tow.

\* \* \* \* \*